United States Patent [19]

Murchison

[11] Patent Number: 4,539,334

[45] Date of Patent: Sep. 3, 1985

[54] SELECTIVE POISONING OF FISCHER-TROPSCH CATALYSTS

[75] Inventor: Craig B. Murchison, Midland, Mich.

[73] Assignee: The Dow Chemical Company, Midland, Mich.

[21] Appl. No.: 550,852

[22] Filed: Nov. 14, 1983

[51] Int. Cl.$^3$ .................................................. C07C 1/04
[52] U.S. Cl. .................................... 518/717; 518/714; 518/715; 518/716; 518/718; 518/719; 518/721
[58] Field of Search ............... 518/717, 718, 719, 721, 518/714, 715, 716

[56] References Cited

U.S. PATENT DOCUMENTS

| | | | |
|---|---|---|---|
| 2,542,464 | 2/1951 | Black et al. | 518/718 |
| 2,647,138 | 7/1953 | Rottig | 518/717 |
| 2,707,713 | 5/1955 | Mattox | 518/718 |
| 2,731,486 | 1/1956 | Rottig | 518/718 |

FOREIGN PATENT DOCUMENTS 672405  5/1952  United Kingdom ............... 518/719

*Primary Examiner*—Howard T. Mars
*Attorney, Agent, or Firm*—Charles J. Enright

[57] ABSTRACT

A Fischer-Tropsch process comprises contacting hydrogen and carbon monoxide in the presence of a conventional Fischer-Tropsch catalyst in combination with an amount of phosphorus effective to selectively poison the Fischer-Tropsch catalyst so as to improve the selectivity of said catalyst to $C_2$–$C_4$ olefins.

15 Claims, No Drawings

SELECTIVE POISONING OF FISCHER-TROPSCH CATALYSTS

FIELD OF THE INVENTION

This invention relates to Fischer-Tropsch reactions for the production of hydrocarbon and, in particular, $C_2$–$C_4$ hydrocarbons, and more particularly, $C_2$–$C_4$ olefins by the selective poisoning of a conventional Fischer-Tropsch catalyst.

BACKGROUND OF THE INVENTION

The art is replete with examples of Fischer-Tropsch catalytic processes for making hydrocarbons from $H_2$/CO mixtures. These processes yield olefinic aromatic and paraffinic hydrocarbons as well as oxygenated hydrocarbons. Much of this art concerns itself with methods for improving conversion (i.e., the amount of carbon monoxide converted to the above-mentioned products), or methods for improved selectivity (i.e., the amount of carbon converted to a given desired product divided by the total carbon converted).

Many examples in the art relate to improvements in the selectivity to a desirable product such as ethylene or materials which can be thermally cracked to ethylene. Materials which can be thermally cracked to ethylene include $C_2$–$C_4$ paraffinic hydrocarbons and $C_3$–$C_4$ olefinic hydrocarbons.

It is desirable to maximize the yield of ethylene in this process subgroup because losses occur when thermally cracking the other hydrocarbons to ethylene. An example of a process for maximizing the $C_2$–$C_4$ olefins is U.S. Pat. No. 4,199,522, which is incorporated herein by reference. This patent discloses a method for increasing the selectivity to $C_2$–$C_4$ olefins by using a catalyst with less than 100 $m^2$/g surface area and comprising at least one member of the group of metals, oxides or sulfides of molybdenum, tungsten, rhenium, ruthenium, nickel, palladium, rhodium, osmium, iridium, and platinum, and at least one member of the group of hydroxides, oxides or salts of alkali and alkaline earth metals; which catalyst may optionally be on a support comprising alumina, carbon, silica, zirconia, zircon, titanium dioxide, magnesia, or mixtures thereof.

An alternative to the above method is to selectively poison a conventional Fischer-Tropsch catalyst. The Fischer-Tropsch synthesis combines many types of reactions. Exemplary reactions include the formation and destruction of carbon-to-oxygen bonds, the formation and destruction of olefinic bonds, the formation of carbon-to-carbon bonds to yield polymers of methylene groups. An option to improve the yield of $C_2$–$C_4$ olefins is to selectively poison the catalyst being used to prevent higher polymerization of the methylene groups.

U.S. Pat. Nos. 2,717,259 and 2,717,260, which are hereby incorporated by reference, describe two alternatives for doing this. The former discloses the addition of halogen to the Fischer-Tropsch reactants. The latter discloses the addition of halogen and sulfur to the Fischer-Tropsch reactants in combination. Both improvements increase the selectivity to $C_2$–$C_4$ olefins. However, the improved selectivity has its price.

The halogen does not react irreversibly with the catalyst. The halogen in the form of hydrogen halide is mobile. The hydrogen halide may migrate from the catalyst into the product stream and corrode process equipment. The addition of sulfur to Fischer-Tropsch catalyst may substantially decrease the conversion. While the selectivity to $C_2$–$C_4$ olefins may be higher, the net yield may be lower because of lowered conversion. If one attempts to restore conversion by raising temperature, the catalyst may degrade by coking and swelling. If one attempts to restore conversion by lowering the space velocity, the $C_2$–$C_4$ olefin production still decreases.

OBJECTS OF THE INVENTION

It is an object of the invention to improve the selectivity of a conventional Fischer-Tropsch process and catalyst to $C_2$–$C_4$ olefins by selective poisoning of the Fischer-Tropsch catalyst. It is an alternative object of the invention to provide a process for formation of $C_2$–$C_4$ olefins by the hydrogenation of carbon monoxide over a Fischer-Tropsch catalyst which has been selectively poisoned to enhance the $C_2$–$C_4$ olefin yield. It is a preferred object of the invention to selectively poison a Fischer-Tropsch catalyst to enhance the $C_2$–$C_4$ olefin yield with an additive that does not also yield corrosive products.

SUMMARY OF THE INVENTION

One or more of these objects and other objects of the invention are achieved by a Fischer-Tropsch process comprising contacting hydrogen and carbon monoxide in the presence of a conventional Fischer-Tropsch catalyst in combination with an amount of phosphorus effective to improve the selectivity of the catalyst to $C_2$–$C_4$ olefins.

A feature of the invention is a combination of a conventional Fischer-Tropsch catalyst with sufficient phosphorus to enhance the selectivity to $C_2$–$C_4$ olefins. The higher selectivity may be obtained in a single stage reaction.

An advantage of the invention over the prior art selective poisons is that phosphorus does not form species corrosive to the equipment used in the process.

DETAILED DESCRIPTION OF THE INVENTION

The hydrogen and carbon monoxide required for this process can be obtained by methods known in the art. Examples are gasification of hydrocarbonaceous materials such as coal, high specific gravity oils, or natural gas; as a by-product of partial combustion cracking; or through the water-gas shift reaction. The two components may also be generated separately and combined for the subject reaction. The molar ratio of hydrogen to carbon monoxide in the feed gas ranges generally from about 0.25 to about 4.0, preferably from about 0.5 to about 1.5 and most preferably 1.0 or less.

The hydrocarbons produced include paraffinic, olefinic and aromatic hydrocarbons as well as oxygenated hydrocarbon compounds such as alcohols, aldehydes, ketones and acids. In general, the use of the catalyst described favors production of lower molecular weight paraffins and olefins and, particularly $C_2$–$C_4$ olefins.

Process conditions can vary over a broad range. Generally, they will fall within the bounds known to the art. The pressure can vary from atmospheric to about 1500 psig and preferably from about 150 psig to about 500 psig. The process temperature ranges from about 150° C. to about 500° C. and preferably from about 200° C. to about 300° C.

Conversion levels may be varied to values known in the art. However, since it is known that to some extent selectivity is a function of conversion, it is preferred that the conversion levels vary from about 20 percent to about 70 percent based on conversion of carbon monoxide. Generally, lower conversions give higher selectivity to lower molecular weight hydrocarbons.

Preferred methods for lowering conversion include increasing the space velocity and lowering temperature. Space velocities preferably are less than about 3,000 volumes of total gas including recycle per volume of catalyst.

Conventional catalysts may be used in this process. Examples of such catalysts are described by M. E. Dry, The Fischer-Tropsch Synthesis, Chapter 4, Catalysis Schience & Technology, Springer Verlag, New York, 1981, which is incorporated herein by reference.

Preferred conventional Fischer-Tropsch catalysts include the Group VIII metals, and most preferably iron. The primary catalytic ingredient may be used in combination with additional known components such as vanadium, manganese, zinc, cerium, titanium, and rare earth or alkali promoters. Alkali metals include lithium, sodium, potassium, and rubidium.

Catalysts may be prepared by known techniques. Exemplary preparations are included in the M. E. Dry reference cited above and the references cited therein. The preferred catalysts are prepared from pigment grade powders of primary and secondary catalytic materials with small amounts of promoter such as the alkali metals. Mixing may be carried out in dry state, such as with a Lancaster mixer, a ball mill, or the components may be blended with water or an organic medium to given a homogeneous cream, which is dried and used. If a catalyst is to be pelleted, the dried cake from the previous step is ground, screened and pelleted using conventional apparatus. Alternatively, water may be added to the dried mixture to form a stiff paste which may then be forced through the die of an extruder or on a small scale through a large laboratory syringe to form a noodle which is then cut into the desired size. The resulting green pellets may be sintered at high temperatures, for example, 1000° C., to form the catalyst pellets. The atmosphere during the sintering step may be an inert such as helium or nitrogen, air or just the residual atmosphere formed on heating up the catalyst pellets with no gas purge.

It is recognized that more active catalysts may be prepared by precipitation, but this may be neither necessary nor desirable. For some catalytic materials, for example, iron, too high a specific activity is more often the case. Accordingly, the more active catalysts must have their activity artificially lowered by dilution or poisoning. Additionally, it is often desirable to use as high a temperature in the Fischer-Tropsch reaction as is compatible with low carbon deposition on the catalyst to favor light hydrocarbon formation. Therefore, again high activity is less desirable. Additionally, catalysts made by such agglomerations are easier to make than going through a precipitation with large volumes of solutions.

Phosphorus is added to the Fischer-Tropsch reaction by either addition to the catalyst as it is made or by addition of a volatile phosphorus compound to the hydrogen and carbon monoxide reactants. Phosphorus may be added in free or combined form. When the phosphorus is added as part of the initial catalyst loading to the reactor, it may be added to the catalyst after it is made or may be added to the catalyst precursors. Phosphorus may be added directly to the reaction along with the feeds as a volatile phosphorus compound. Elemental phosphorus may be used, but more preferably phosphorus is used in the form of a volatile organic phosphorus compound. Suitable phosphorus compounds include the organic phosphates, phosphites, phosphines. Exemplary materials are alkyl phosphates, alkyl phosphites, alkyl phosphines, etc. Specific examples include tributyl phosphate, trimethyl phosphite, and phosphine.

Based on elemental phosphorus, the appropriate amount of the phosphorus additive to be used is that which is effective to selectively poison the catalyst and increase the selectivity to $C_2$–$C_4$ olefins. Preferably, the amount of phosphorus used is that which will increase the selectivity to $C_2$–$C_4$ olefins by 10 percent over the unmodified value. When the phosphorus is added to the feed, it may be added at a single time at which it is added at a level sufficient to give from about 2 milligrams to about 40 milligrams of phosphorus per gram of catalyst and preferably from about 6 milligrams to about 20 milligrams of phosphorus per gram of catalyst.

In order to obtain improved selectivities to $C_2$–$C_4$ olefins it is not necessary for the catalyst to be arrayed in multiple serial beds. It may be placed in a single bed or in multiple parallel beds.

The following examples are considered illustrative of the surprising results obtained with the process of the invention. Elements and the catalyst are given as weight percent of the components added prior to water addition and treatments of the catalyst such as calcination and reduction which tend to alter the final composition.

Subscripts, e.g., the 1 in $C_1$, in all examples indicate the number of carbon atoms. Hydrocarbon analyses are reported in carbon mole percent in all examples. "Carbon mole percent" is defined as 100 times the moles of carbon present in the hydrocarbon fraction of interest divided by the total moles of carbon in the product hydrocarbon. For example, if one mole of ethylene is found in the $C_2$ fraction, this is counted as 2 moles of carbon. The term "product hydrocarbon" excludes any carbon dioxide produced. In the examples, an apparatus is utilized, which includes in sequential order, three high pressure gas bottles, a manifold, and reactors equipped on the downstream side with a fine metering valve, a rotameter, a sampling manifold, and gas chromatograph. The two bottles contain mixtures of hydrogen, carbon monoxide and nitrogen. The mixtures permit varying of the hydrogen to carbon monoxide ratio from about 0.5 to about 3.0. The third bottle contains hydrogen. Each bottle is independently connected to the manifold. The manifold is constructed such that any of the three bottles may be used to feed the reactor. Through the sampling manifold, the product of each reactor may be piped to the gas chromatograph for analysis. The catalysts are loaded into ½-inch internal diameter reactors and are reduced in hydrogen before being used. The reactors are then brought to operating temperature in the presence of hydrogen. Next, feed from the high pressure gas bottle containing hydrogen and carbon monoxide is allowed to flow through the manifold to the reactor. Pressure, flow and temperature are adjusted to operating values.

EXAMPLE 1

The catalyst is made by physically mixing pigment grade powders in the following proportions: iron oxide ($Fe_2O_3$) 85.5 percent; titanium dioxide 7.6 percent; potassium carbonate 1.9 percent; and 5 percent graphite as a pelleting lubricant. After mixing, the resulting powder is pelleted in a pellet press. The pellets are then calcined at 1000° C. and subsequently reduced in hydrogen at 425° C. Yields are set out in the following Table I, wherein Comparison A sets out the yields in the absence of added phosphate and Example 1 demonstrates the results of the addition of 400 micro-liters of tributyl-phosphate by injection into the reactant gas stream. The weight of the catalyst was 7.8 grams and it occupied 4 cc. The results show that addition of phosphorus increases the selectivity to $C_2$-$C_4$ olefins and decreases the selectivity to $C_5^+$ oil.

TABLE I

|  | Comparison A | Example 1 |
| --- | --- | --- |
| Temperature (°C.) | 280° C. | 300° C. |
| Pressure (psig) | 150 | 300 |
| GHSV (hr$^{-1}$) | 1000 | 550 |
| H$_2$/CO (molar ratio) | 1.0 | 1.0 |
| CO Conversion (%) | 40 | 39 |
| Methane | 11.7 | 19.6 |
| Ethylene | 4.1 | 7.5 |
| Propylene | 10.3 | 18.7 |
| Butylenes | 8.7 | 12.5 |
| Total C$_2$-C$_4$ Olefins | 23.1 | 38.7 |
| Ethane | 7.6 | 10.5 |
| Propane | 5.7 | 3.8 |
| Butanes | 2.2 | 2.0 |
| Total C$_2$-C$_4$ Paraffins | 15.5 | 16.3 |
| % Olefins in C$_2$-C$_4$ Product (%) | 60 | 70 |
| C$_5^+$ Oil | 49.7 | 25.4 |

EXAMPLE 2

A catalyst made with the same proportions of ingredients and by the same method of Example 1 is compared with and without a small addition of phosphorus. Comparison B contains no added phosphorus. Example 2 contains 3 mg phosphorus per gram of catalyst added as trimethyl phosphite. Results are shown in Table II. The results in Table II show that the $C_2$ and $C_3$ olefin selectivity is increased when a very low level of phosphorus is added to the conventional Fischer-Tropsch catalyst. Similar to Table I, these results show that a small amount of phosphorus added to a conventional Fischer-Tropsch catalyst can increase the ratio of olefins to paraffins in the $C_2$-$C_4$ range, increase the $C_2$-$C_4$ selectivity, and decrease the $C_5^+$ oil selectivity.

TABLE II

|  | Comparison B | Example 2 |
| --- | --- | --- |
| Temperature (°C.) | 293 | 292 |
| Pressure (psig) | 285 | 295 |
| GHSV (hr$^{-1}$) | 687 | 476 |
| H$_2$/CO (molar ratio) | 0.81 | 0.81 |
| CO Conversion (%) | 32 | 34 |
| Methane | 15.0 | 21.4 |
| Ethylene | 3.9 | 5.8 |
| Propylene | 11.7 | 14.8 |
| Butenes | 11.3 | 10.5 |
| Total C$_2$-C$_4$ Olefins | 26.9 | 31.1 |
| Ethane | 11.5 | 10.7 |
| Propane | 8.6 | 6.6 |
| Butane | 6.8 | 7.2 |
| Total C$_2$-C$_4$ Paraffins | 26.9 | 24.5 |
| % Olefins in C$_2$-C$_4$ Fraction | 50 | 56 |
| C$_5^+$ Oil | 35.1 | 22.3 |

Although the invention has been described in considerable detail, it must be understood that such detail is for the purpose of illustration only and many variations and modifications can be made by one skilled in the art without departing from the spirit and scope of the invention.

What is claimed is:

1. A Fischer-Tropsch process comprising contacting hydrogen and carbon monoxide in the presence of a conventional Fischer-Tropsch catalyst in combination with an amount of phosphorus in the absence of halogen effective to improve the selectivity of the catalyst to $C_2$-$C_4$ olefins by adding a volatile phosphorus compound to the carbon monoxide and hydrogen reactants.

2. The process of claim 1 wherein the catalyst contains iron.

3. The process of claim 2 wherein the catalyst is primarily iron.

4. The process of claim 2 wherein the catalyst contains an alkali metal promoter.

5. The process of claim 4 wherein the alkali metal promoter is potassium.

6. The process of claim 1 wherein the phosphorus compound is phosphorus or an organic phosphate, phosphite, phosphine or a mixture thereof.

7. The process of claim 6 wherein the amount of phosphorus in the phosphorus/catalyst combination is at least about two milligrams of phosphorus per gram of catalyst.

8. The process of claim 7 wherein the amount of phosphorus is less than about 40 milligrams per gram of catalyst.

9. The process of claim 1 wherein the catalyst is arrayed in a single bed or in multiple parallel beds.

10. The process of claim 1 wherein the contacting is carried out at a pressure of from about 150 to about 500 psig.

11. The process of claim 1 wherein the contacting is carried out at a temperature of from about 150° C. to about 500° C.

12. The process of claim 11 wherein the temperature is from about 200° C. to about 300° C.

13. The process of claim 1 wherein the contacting is carried out at a gas hourly space velocity of less than about 3,000 volumes of total gas including any recycle per volume of catalyst.

14. The process of claim 1 wherein the hydrogen and carbon monoxide are present at a molar ratio of from about 0.5 H$_2$/CO to about 1.5 H$_2$/CO.

15. The process of claim 14 wherein the ratio is less than about 1.0.

* * * * *